US008689785B2

(12) United States Patent
Wright et al.

(10) Patent No.: US 8,689,785 B2
(45) Date of Patent: Apr. 8, 2014

(54) DISPENSING APPARATUS

(75) Inventors: Andrew Wright, Norfolk (GB); Martin Swain, Norfolk (GB); William Southby, Norfolk (GB); Richard Warby, Norfolk (GB)

(73) Assignee: Consort Medical PLC, Hemel Hempstead (GB)

( * ) Notice: Subject to any disclaimer, the term of this patent is extended or adjusted under 35 U.S.C. 154(b) by 1495 days.

(21) Appl. No.: 11/798,936

(22) Filed: May 17, 2007

(65) Prior Publication Data

US 2007/0284383 A1    Dec. 13, 2007

(30) Foreign Application Priority Data

May 26, 2006  (GB) .................................. 0610538.1

(51) Int. Cl.
*A61M 11/00* (2006.01)

(52) U.S. Cl.
USPC ............ 128/200.14; 128/200.23; 128/205.23; 222/36

(58) Field of Classification Search
USPC ............ 128/200.14, 200.18, 200.23, 203.12, 128/203.15, 203.23, 205.23; 222/32, 36, 222/162; 116/307–309, 317, 318
See application file for complete search history.

(56) References Cited

U.S. PATENT DOCUMENTS

| | | | |
|---|---|---|---|
| 3,178,110 A | 4/1965 | Knecht et al. | |
| 3,622,053 A | 11/1971 | Ryden | |
| 3,994,421 A | 11/1976 | Hansen | |
| 4,414,972 A | 11/1983 | Young et al. | |
| 4,563,574 A | 1/1986 | Dreyer et al. | |
| 4,565,302 A * | 1/1986 | Pfeiffer et al. | 222/38 |
| 4,841,964 A | 6/1989 | Hurka et al. | |
| 5,174,473 A * | 12/1992 | Marelli | 222/38 |
| 5,522,378 A | 6/1996 | Ritson et al. | |
| 5,562,219 A * | 10/1996 | de Pous et al. | 215/274 |
| 5,565,861 A | 10/1996 | Mettler et al. | |

(Continued)

FOREIGN PATENT DOCUMENTS

| | | |
|---|---|---|
| CA | 2 392 466 A1 | 6/1997 |
| DE | 805 817 | 5/1951 |

(Continued)

OTHER PUBLICATIONS

Search Report under Section 17 for Application No. GB0411384.1 dated Aug. 27, 2004.

(Continued)

*Primary Examiner* — Steven Douglas
(74) *Attorney, Agent, or Firm* — Smith, Gambrell & Russell, LLP

(57) ABSTRACT

The present invention provides dispensing apparatus for delivering metered doses of product from a pressurized dispensing container comprising:
a housing for receiving a pressurized dispensing container;
a dose counting mechanism comprising indication means for displaying to a user an indication associated with the number or quantity of doses dispensed from, or the number or quantity of doses remaining in, the received pressurized dispensing container;
the dose counting mechanism further comprising an indexing mechanism for advancing the indication means on actuation of the received pressurized dispensing container;
wherein the dispensing apparatus comprises an indexing member capable of moving within the housing in sync with the received pressurized dispensing container;
wherein on actuation of the received pressurized dispensing container in a normal mode of operation the indexing member is able to interface with the indexing mechanism to apply a force to the indexing mechanism sufficient to incrementally advance the indication means.

18 Claims, 11 Drawing Sheets

(56) References Cited

U.S. PATENT DOCUMENTS

| | | | |
|---|---|---|---|
| 5,772,080 | A | 6/1998 | De Pous et al. |
| 5,808,337 | A | 9/1998 | Weimer et al. |
| 5,833,088 | A | 11/1998 | Kladders et al. |
| 5,871,007 | A | 2/1999 | Clark, Jr. |
| 5,984,122 | A | 11/1999 | Barker et al. |
| 5,988,496 | A * | 11/1999 | Bruna .................... 235/91 R |
| 6,189,739 | B1 | 2/2001 | von Schuckmann |
| 6,234,168 | B1 | 5/2001 | Bruna |
| 6,360,739 | B1 | 3/2002 | Rand et al. |
| 7,322,352 | B2 | 1/2008 | Minshull et al. |
| 7,448,342 | B2 | 11/2008 | Von Schuckmann |
| 7,464,708 | B2 | 12/2008 | Marx |
| 7,500,444 | B2 | 3/2009 | Bonney et al. |
| 7,543,582 | B2 | 6/2009 | Lu et al. |
| 7,571,726 | B2 | 8/2009 | Parker |
| 7,587,988 | B2 | 9/2009 | Bowman et al. |
| 7,827,984 | B2 | 11/2010 | Von Schuckmann |
| 7,828,172 | B2 | 11/2010 | Stradella et al. |
| 7,832,351 | B2 * | 11/2010 | Bonney et al. .................. 116/311 |
| 2003/0015191 | A1 | 1/2003 | Armstrong et al. |
| 2003/0209239 | A1 | 11/2003 | Rand et al. |
| 2004/0065326 | A1 | 4/2004 | MacMichael et al. |
| 2004/0089292 | A1 | 5/2004 | Pollet et al. |
| 2004/0094147 | A1 | 5/2004 | Schyra et al. |
| 2004/0139964 | A1 | 7/2004 | Langford |
| 2004/0149773 | A1 | 8/2004 | Ouyang et al. |
| 2004/0211420 | A1 | 10/2004 | Minshull et al. |
| 2004/0222237 | A1 | 11/2004 | Blacker et al. |
| 2007/0181120 | A1 | 8/2007 | Wright et al. |
| 2007/0210102 | A1 | 9/2007 | Stradella et al. |
| 2007/0246042 | A1 | 10/2007 | Purkins et al. |
| 2008/0017192 | A1 | 1/2008 | Southby et al. |
| 2008/0265198 | A1 | 10/2008 | Warby |
| 2009/0139516 | A1 | 6/2009 | Augustyn et al. |

FOREIGN PATENT DOCUMENTS

| | | |
|---|---|---|
| DE | 1237 820 | 3/1967 |
| DE | 27 51 045 | 7/1978 |
| EP | 0 227 510 | 7/1987 |
| EP | 1369139 A1 * | 12/2003 |
| EP | 1 787 668 | 5/2007 |
| EP | 1787668 A1 * | 5/2007 |
| FR | 2 857 770 A1 | 1/2005 |
| GB | 2372542 | 8/2002 |
| GB | 2414187 A * | 11/2005 |
| WO | 93/24167 | 12/1993 |
| WO | 99/36115 | 7/1999 |
| WO | 99/57019 | 11/1999 |
| WO | 01/28887 | 4/2001 |
| WO | 02/04056 | 1/2002 |
| WO | 02/067844 | 9/2002 |
| WO | 03/086518 | 10/2003 |
| WO | 04/001664 A1 | 12/2003 |
| WO | 2004/001664 A1 | 12/2003 |
| WO | 2004/026380 | 4/2004 |
| WO | 2004/026380 A2 | 4/2004 |
| WO | WO 2004056416 A1 * | 7/2004 |
| WO | 2004/089451 A1 | 10/2004 |
| WO | 2005/044354 | 5/2005 |
| WO | 2005/060535 | 7/2005 |
| WO | WO 2005060535 A2 * | 7/2005 |
| WO | 2005/079727 | 9/2005 |
| WO | 2005/113044 | 12/2005 |
| WO | WO 2005/114563 A1 | 12/2005 |
| WO | WO 2005113044 A1 * | 12/2005 |
| WO | 2006/051006 | 5/2006 |
| WO | 2006/054083 | 5/2006 |

OTHER PUBLICATIONS

European Search Report for Application No. EP 09 00 8924 dated Aug. 18, 2009.

European Search Report for Application No. EP 08 00 3115 dated Feb. 18, 2009.

European Search Report for Application No. EP 07 25 1812 dated Jul. 23, 2007.

Search Report under Section 17 issued in GB0523716.9, dated Mar. 20, 2006.

Further Search Report under Section 17 issued in GB0523716.9, dated Sep. 19, 2006.

Combined Search and Examination Report under Sections 17 and 18(3) corresponding to Application No. GB0813133.6 dated Aug. 26, 2008.

Combined Search and Examination Report under Sections 17 and 18(4) corresponding to Application No. GB0813131.0 dated Aug. 27, 2008.

Partial European Search Report for Application No. EP 07 25 1278 dated Nov. 29, 2012.

* cited by examiner

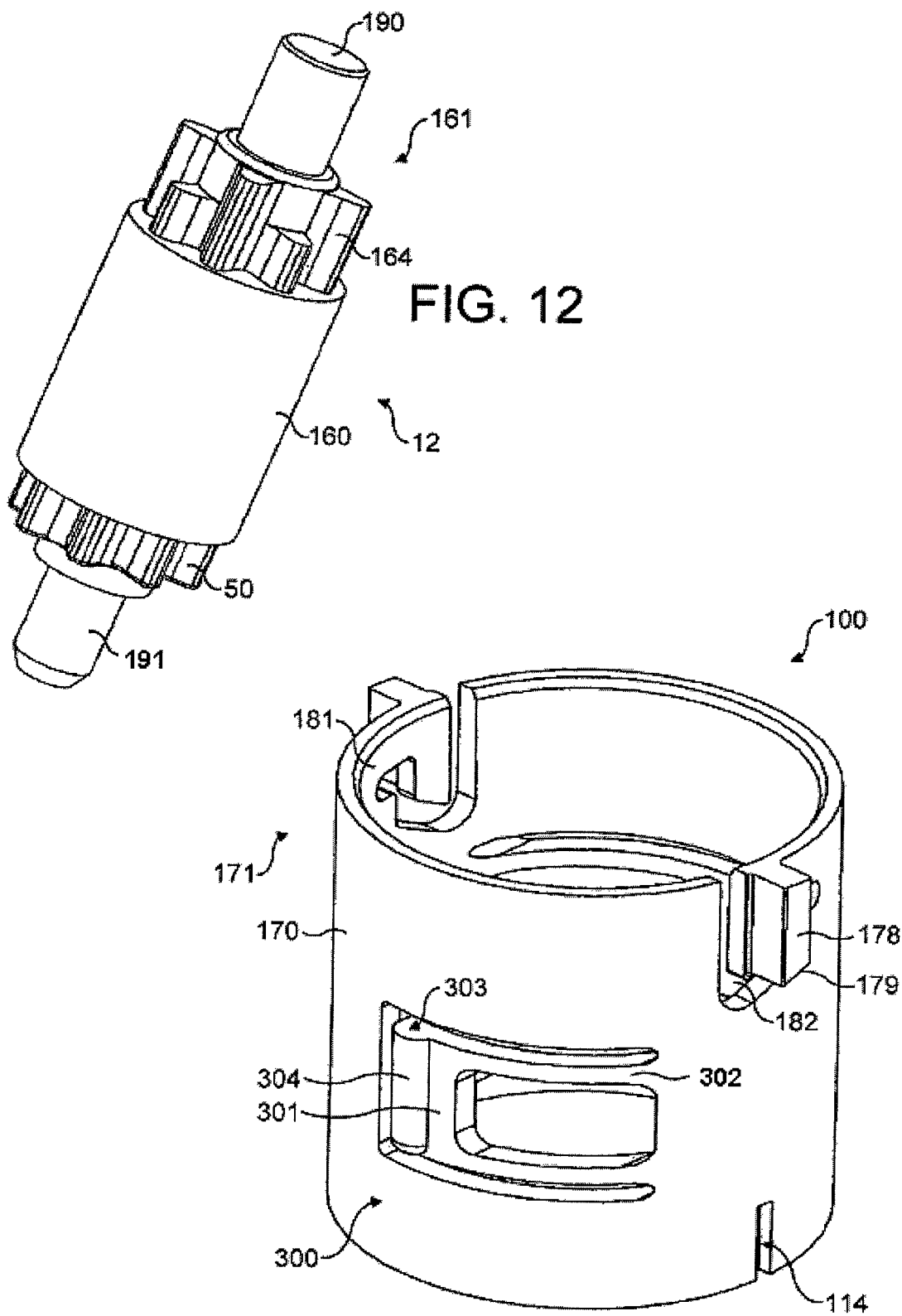

DISPENSING APPARATUS

This invention relates to dispensing apparatus having integral dosage counting devices which require an axial force for actuation.

It has been recognised that there is a need to provide accurate information to a user of a dose-dispensing delivery apparatus, such as a pressurised metered dose inhaler, concerning the number of doses delivered from, or remaining in, the dispensing apparatus. Without such information, there is a danger that a user will forget how many doses have been delivered and hence take a greater or fewer number of doses than are required. There is also a danger that a user may be unaware that the dispensing container of the dispensing apparatus is empty or close to empty. This is especially dangerous where the dispensing apparatus is for use in delivering medicinal compounds for the treatment of chronic or acute symptoms, for example, as in the case of a pressurised metered dose inhaler used for treating asthmatic reactions.

It is known to provide a dispensing apparatus with a dose counting device. Typically such dose counting devices are triggered by movement of the dispensing container wherein the movement either directly or indirectly provides the motive force for incrementing or decrementing the dose counting device. In order for a dose counting device to be accurate it must be designed not to under-count the number of doses dispensed from the dispensing container, otherwise a user may be misled into thinking that the dispensing apparatus has a greater number of remaining doses than is actually the case. There has therefore been a desire to develop dose counting devices where movement of the dispensing container into its actuated position in the dispensing apparatus is not possible without incrementing or decrementing the dose counter device. In this way under-counting is prevented. However, a disadvantage of such dispensing apparatus is that actuation of the dispensing container is not possible if the dose counting device should inadvertently jam or become inoperative for some other reason. There is then the danger that a user would not be able to actuate the dispensing container despite there being available doses therein.

There can also be a problem with known mechanical dosage counters in that they are prone to accidentally incrementing if the apparatus is dropped due to impact forces imparted on the counting mechanism.

Mechanical dose counters can also be difficult to manufacture so that they work reliably. One problem is that a mechanical dose counter typically requires a number of components which must be accurately located relative to one another during assembly to ensure that over-counting or under-counting is not experienced. This can lead to a requirement for very strict manufacturing tolerances which can make manufacture expensive.

According to the present invention there is provided dispensing apparatus for delivering metered doses of product from a pressurised dispensing container comprising:

a housing for receiving a pressurised dispensing container;

a dose counting mechanism comprising indication means for displaying to a user an indication associated with the number or quantity of doses dispensed from, or the number or quantity of doses remaining in, the received pressurised dispensing container;

the dose counting mechanism further comprising an indexing mechanism for advancing the indication means on actuation of the received pressurised dispensing container;

wherein the dispensing apparatus comprises an indexing member capable of moving within the housing in sync with the received pressurised dispensing container;

wherein on actuation of the received pressurised dispensing container in a normal mode of operation the indexing member is able to interface with the indexing mechanism to apply a force to the indexing mechanism sufficient to incrementally advance the indication means;

wherein in the eventuality that the indexing mechanism or the indication means is jammed so as to prevent advancement, the indexing member and the indexing mechanism are enabled to move relative to one another in such a way to allow the indexing member to bypass the indexing mechanism to allow actuation of the received pressurised dispensing container.

In this way the dispensing apparatus may advantageously still be operated when parts of the counting mechanism may have become jammed or otherwise inoperative.

The indexing mechanism may move to achieve the bypass. The indexing mechanism may be able to flex to allow the indexing member to bypass the indexing mechanism to allow actuation of the received pressurised dispensing container.

Alternatively, the indexing member may move to achieve the bypass.

The indexing member may be able to slide, pivot, retract or similar to bypass the indexing mechanism to allow actuation of the received pressurised dispensing container.

Preferably in the eventuality that the indexing mechanism or the indication means is jammed so as to prevent advancement the indexing mechanism is capable of applying a force to the indexing member sufficient to flex the indexing member such that the indexing member is able to bypass the indexing mechanism.

The indexing member may exhibit a degree of inherent flexibility.

The indexing member may flex elastically as it bypasses the indexing mechanism.

Preferably, the indexing member is capable of moving along a longitudinal axis of the housing in sync with the received pressurised dispensing container.

In one embodiment the longitudinal movement of the indexing member interfaces with the indexing mechanism to produce a rotational movement of the indication means about the longitudinal axis.

Preferably the indexing member comprises an elongate portion aligned substantially with the longitudinal axis of the housing.

Preferably flexure of the elongate portion of the indexing member allows the indexing member to move out of alignment with the longitudinal axis of the housing to allow bypass of the indexing mechanism.

The indexing member may comprise a cantilevered portion having a free distal end which interfaces in use with the indexing mechanism.

The cantilevered portion of the indexing member may depend from a flexure point of the dispensing apparatus.

The apparatus may further comprise a sleeve for receiving in use the pressurised dispensing container.

Preferably the indexing member is joined to or formed as part of the sleeve.

The indexing member may comprise a cantilevered portion having a free distal end which interfaces in use with the indexing mechanism, the indexing member depending from a flexure point of the dispensing apparatus, wherein a void space is provided around the cantilevered portion to accommodate flexure of the indexing member.

The dose counting mechanism may comprise one or more annular members.

The one or more annular members may be orientated for rotation about the longitudinal axis of the housing.

In use, the pressurised dispensing container may be received within the housing such that the one or more annular members surround the pressurised dispensing container.

The indexing mechanism may comprise a plurality of angled teeth which interface with the indexing member on longitudinal movement of the indexing member to produce rotation of the one or more annular members.

Preferably the indexing member is formed from acetal, ABS or nylon.

Preferably the sleeve is formed from acetal, ABS or nylon.

The present invention also provides dispensing apparatus for delivering metered doses of product from a pressurised dispensing container comprising:

a housing for receiving a pressurised dispensing container;

a dose counting mechanism comprising indication means for displaying to a user an indication associated with the number or quantity of doses dispensed from, or the number or quantity of doses remaining in, the received pressurised dispensing container;

the dose counting mechanism further comprising an indexing mechanism for advancing the indication means on actuation of the received pressurised dispensing container;

wherein the dispensing apparatus comprises an indexing member capable of moving within the housing in sync with the received pressurised dispensing container;

wherein on actuation of the received pressurised dispensing container the indexing member is able to interface with the indexing mechanism to apply a force to the indexing mechanism sufficient to incrementally advance the indication means;

wherein the indexing member has a degree of inherent flexibility such that in the event of the dispensing apparatus suffering a sudden impact the indexing member is able to flex under impact loading to thereby lessen the chances of damaging the indexing mechanism.

Advantageously, the apparatus is better able to cope with sudden impacts without leading to damage of the indexing mechanism, in particular damage to the teeth of the annular members that preferably make up a part of the indexing mechanism.

The indexing member may comprise a cantilevered portion having a free distal end which interfaces in use with the indexing mechanism.

The cantilevered portion of the indexing member may depend from a flexure point of the dispensing apparatus.

The apparatus may further comprises a sleeve for receiving in use the pressurised dispensing container.

Preferably the indexing member is joined to or formed as part of the sleeve.

The indexing member may comprise a cantilevered portion having a free distal end which interfaces in use with the indexing mechanism, the indexing member depending from a flexure point of the dispensing apparatus, wherein a void space is provided around the cantilevered portion to accommodate flexure of the indexing member.

The dose counting mechanism may comprise one or more annular members.

The one or more annular members may be orientated for rotation about the longitudinal axis of the housing.

In use, the pressurised dispensing container may be received within the housing such that the one or more annular members surround the pressurised dispensing container.

The indexing mechanism may comprise a plurality of angled teeth which interface with the indexing member on longitudinal movement of the indexing member to produce rotation of the one or more annular members.

Preferably the indexing member is formed from acetal, ABS or nylon.

Preferably the sleeve is formed from acetal, ABS or nylon.

The present invention further provides dispensing apparatus for delivering metered doses of product from a pressurised dispensing container comprising:

a housing for receiving a pressurised dispensing container;

a dose counting mechanism comprising indication means for displaying to a user an indication associated with the number or quantity of doses dispensed from, or the number or quantity of doses remaining in, the received pressurised dispensing container;

the dose counting mechanism further comprising an indexing mechanism for advancing the indication means on actuation of the received pressurised dispensing container;

wherein the dispensing apparatus comprises first and second indexing members which together act to incrementally advance the indexing mechanism on actuation of the received pressurised dispensing container;

wherein movement of the received pressurised dispensing container in a first direction relative to the indexing mechanism causes the first indexing member to advance the indexing mechanism by a partial increment and also causes a strain to be imparted on the second indexing member;

wherein subsequent movement of the received pressurised dispensing container a second direction, opposed to the first direction, allows the second indexing member to move the indexing mechanism to complete the incremental advancement of the indexing mechanism by recovery of the imparted strain.

Advantageously, the use of two indexing members working together produces a more reliable mechanism with lower manufacturing tolerances.

Preferably the strain imparted on the second indexing member is in a different direction compared to the direction of movement of the first indexing member.

Preferably the strain imparted on the second indexing member is in a direction substantially perpendicular compared to the direction of movement of the first indexing member.

The first indexing member may be moveable parallel to the longitudinal axis of the received pressurised dispensing container.

The strain imparted on the second indexing member may be in a radial direction relative to the received pressurised dispensing container.

The first indexing member may comprise a cantilevered portion having a free distal end which interfaces in use with the indexing mechanism.

The cantilevered portion of the indexing member may comprise an elongate portion running parallel to the longitudinal axis of the received pressurised dispensing container.

The second indexing member may comprise a cantilevered portion having a free distal end which interfaces in use with the indexing mechanism.

The cantilevered portion of the second indexing member may comprise an arcuate portion running around the longitudinal axis of the received pressurised dispensing container.

Preferably a distal end of the second indexing member comprises an outwardly directed projection for engaging the indexing mechanism.

The indexing mechanism may comprise an annular member.

The annular member may comprise a first set of abutment surfaces for engagement with the first indexing member and a second set of abutment surfaces for engagement with the second indexing member.

Preferably the second set of abutment surfaces are formed by a circumferential series of inwardly directed projections of the annular member. The series of inwardly directed projections comprises interspaced peaks and troughs defined by the abutment surfaces.

Preferably a distal end of the second indexing member comprises an outwardly directed projection for engaging the second set of abutment surfaces.

The apparatus may further comprise a sleeve for receiving in use the pressurised dispensing container.

The first and second indexing members may be joined to or formed as part of the sleeve.

The dispensing apparatus may be a pharmaceutical dispensing device, such as, for example, a pulmonary, nasal, or sub-lingual delivery device. A preferred use of the dispensing apparatus is as a pharmaceutical metered dose aerosol inhaler device. The term pharmaceutical, as used herein, is intended to encompass any pharmaceutical, compound, composition, medicament, agent or product which can be delivered or administered to a human being or animal, for example pharmaceuticals, drugs, biological and medicinal products. Examples include antiallergics, analgesics, bronchodilators, antihistamines, therapeutic proteins and peptides, antitussives, anginal preparations, antibiotics, anti-inflammatory preparations, hormones, or sulfonamides, such as, for example, a vasoconstrictive amine, an enzyme, an alkaloid, or a steroid, including combinations of two or more thereof. In particular, examples include isoproterenol [alpha-(isopropylaminomethyl) protocatechuyl alcohol], phenylephrine, phenylpropanolamine, glucagon, adrenochrome, trypsin, epinephrine, ephedrine, narcotine, codeine, atropine, heparin, morphine, dihydromorphinone, ergotamine, scopolamine, methapyrilene, cyanocobalamin, terbutaline, rimiterol, salbutamol, flunisolide, colchicine, pirbuterol, beclomethasone, orciprenaline, fentanyl, and diamorphine, streptomycin, penicillin, procaine penicillin, tetracycline, chlorotetracycline and hydroxytetracycline, adrenocorticotropic hormone and adrenocortical hormones, such as cortisone, hydrocortisone, hydrocortisone acetate and prednisolone, insulin, cromolyn sodium, and mometasone, including combinations of two or more thereof.

The pharmaceutical may be used as either the free base or as one or more salts conventional in the art, such as, for example, acetate, benzenesulphonate, benzoate, bicarbonate, bitartrate, bromide, calcium edetate, camsylate, carbonate, chloride, citrate, dihydrochloride, edetate, edisylate, estolate, esylate, fumarate, fluceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylbromide, methylnitrate, methylsulphate, mucate, napsylate, nitrate, pamoate, (embonate), pantothenate, phosphate, diphosphate, polygalacturonate, salicylate, stearate, subacetate, succinate, sulphate, tannate, tartrate, and triethiodide, including combinations of two or more thereof. Cationic salts may also be used, for example the alkali metals, e.g. Na and K, and ammonium salts and salts of amines known in the art to be pharmaceutically acceptable, for example glycine, ethylene diamine, choline, diethanolamine, triethanolamine, octadecylamine, diethylarnine, triethylamine, 1-amino-2-propanol-amino-2-(hydroxymethyl)propane-1,3-diol, and 1-(3,4-dihydroxyphenyl)-2 isopropylaminoethanol.

The pharmaceutical will typically be one which is suitable for inhalation and may be provided in any suitable form for this purpose, for example as a solution or powder suspension in a solvent or carrier liquid, for example ethanol, or isopropyl alcohol. Typical propellants are HFA134a, HFA227 and dimethyl ether.

The pharmaceutical may, for example, be one which is suitable for the treatment of asthma. Examples include salbutamol, beclomethasone, salmeterol, fluticasone, formoterol, terbutaline, sodium chromoglycate, budesonide and flunisolide, and physiologically acceptable salts (for example salbutamol sulphate, salmeterol xinafoate, fluticasone propionate, beclomethasone dipropionate, and terbutaline sulphate), solvates and esters, including combinations of two or more thereof. Individual isomers such as, for example, R-salbutamol, may also be used. As will be appreciated, the pharmaceutical may comprise of one or more active ingredients, an example of which is flutiform, and may optionally be provided together with a suitable carrier, for example a liquid carrier. One or more surfactants may be included if desired.

Rigid components of the dispensing apparatus may be formed from, for example, from polyester, nylon, acetal or similar.

Preferably, the first and or second indexing members are formed of an elastic material such that imparted strains during normal actuation are recoverable elastically In order that the invention may be fully disclosed, embodiments will now be described, by way of example, with reference to the accompanying drawings, in which:—

FIG. 12 is a perspective view of a cog forming part of the dispensing apparatus of FIG. 8;

FIG. 13 is a perspective view of a sleeve forming part of the dispensing apparatus of FIG. 8;

Figure 1:
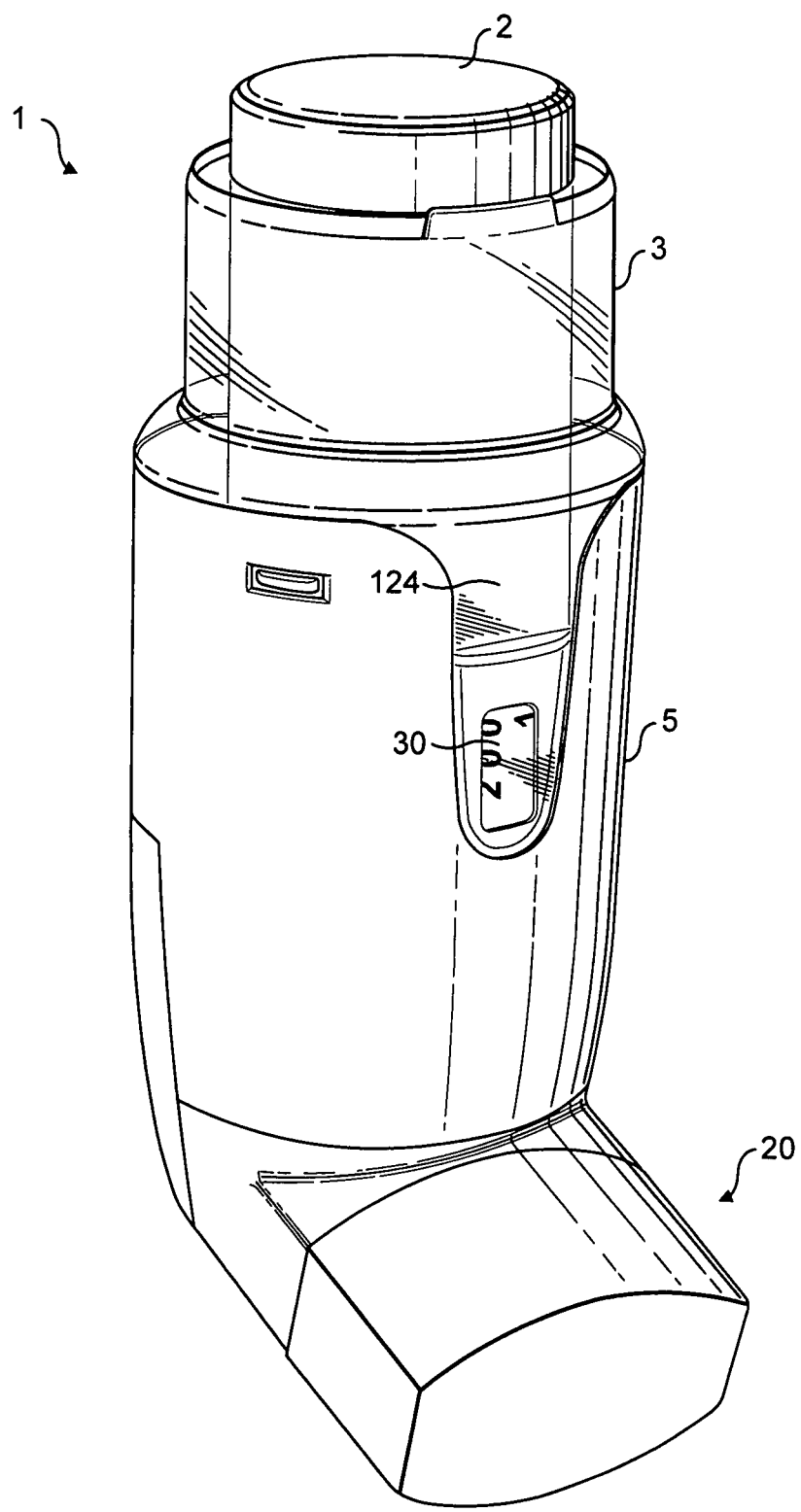
FIG. 1 is a perspective view of a first embodiment of dispensing apparatus according to the present invention.
Figure 2:
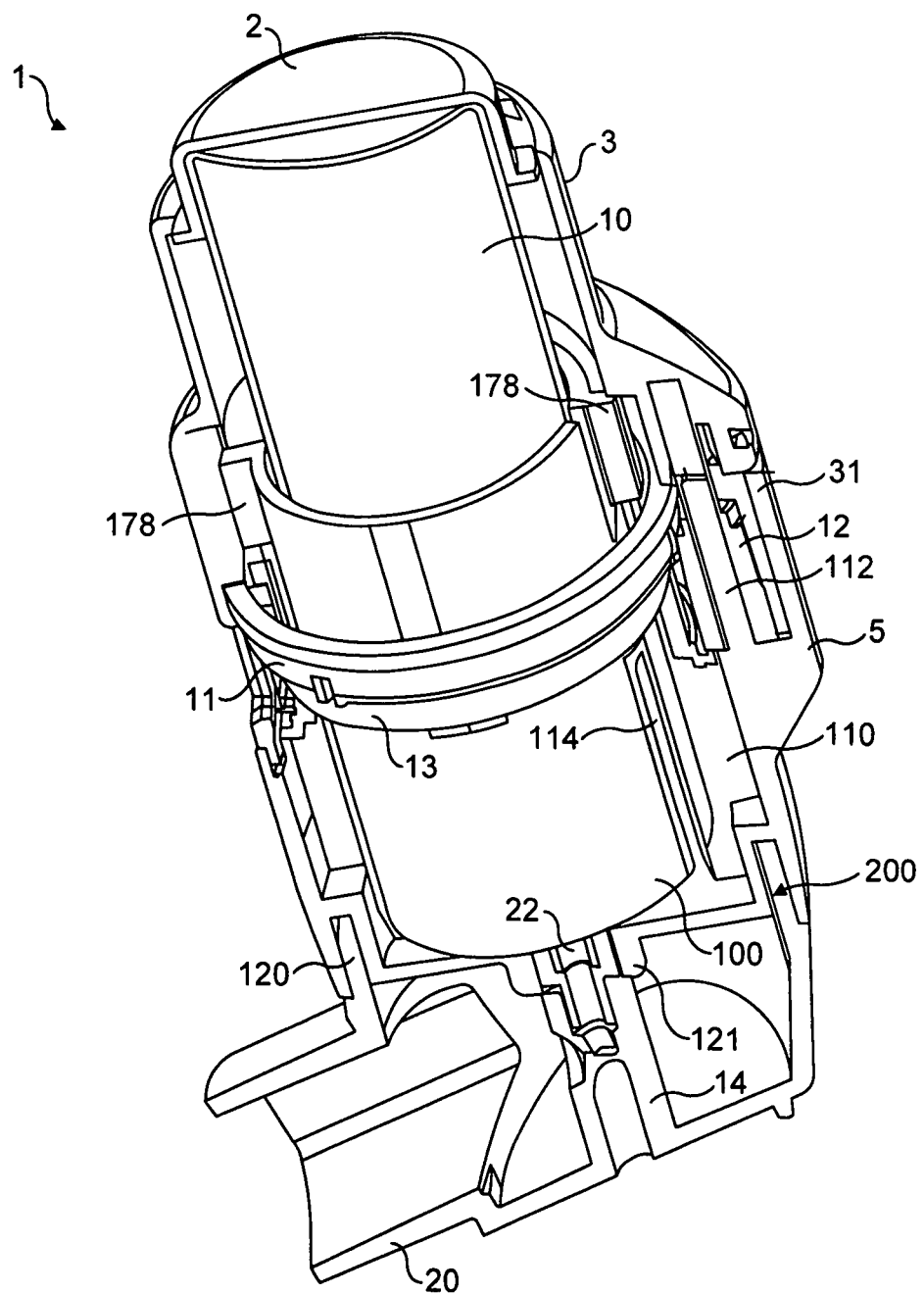
FIG. 2 is a cross-sectional view of the apparatus of FIG. 1.
Figure 3:
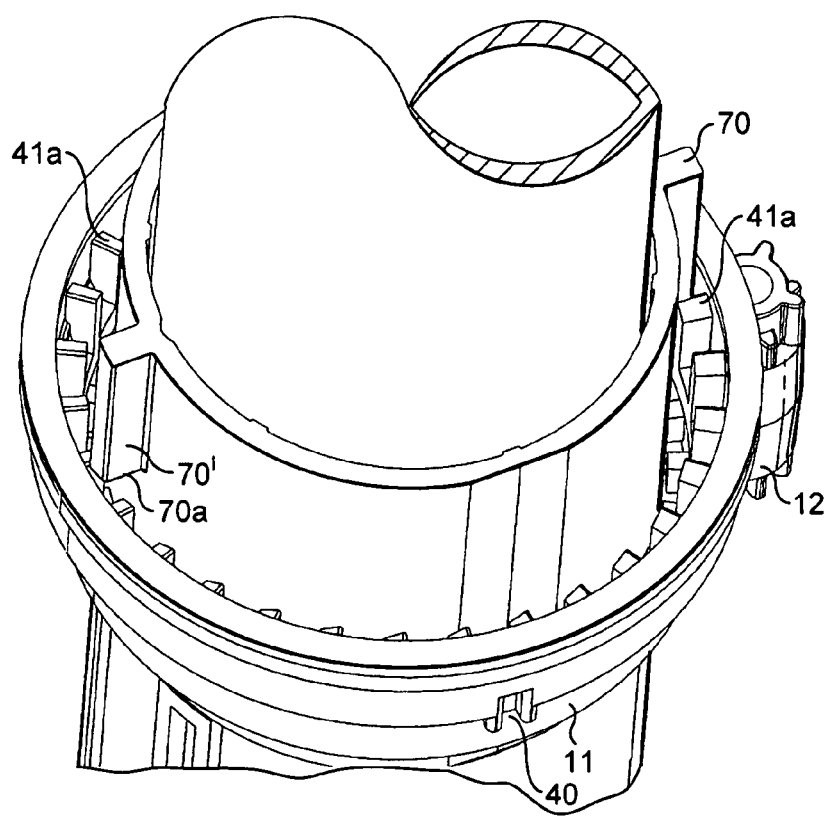
FIG. 3 is a perspective view of various internal features of the dispensing apparatus of FIG. 1.

FIG. 1 shows a dispensing apparatus, indicated generally at 1, having a cap 2, a fixing collar 3, a main body 5 and a detachable mouthpiece 20. A dust cap may be used to cover the mouthpiece 20 when the apparatus is not in use. As shown in FIG. 2, the dispensing apparatus is also provided with first and second number rings 11,13, a cog 12 and a sleeve 100. In use the apparatus receives a pressurised dispensing container 10.

The main body 5, which is substantially cylindrical, comprises an enlarged portion 31, and is open at its upper end. The enlarged portion 31, situated at the upper end thereof,—in relation to the dispensing apparatus—houses the cog 12 and the first and second number rings 11, 13. The number rings 11, 13 rest upon internal projections 110 of the main body 5. Such internal projections 110 provide up-facing surfaces upon which the second number ring 13 may rest and rotate, during use. The first number ring 11 rests and rotates, during use, on top of the second number ring 13. The cog 12 is rotatably mounted within the main body 5 on a cylindrical portion 112 and interacts with both first and second number rings 11, 13. As can be seen, the axis of rotation of the cog 12 is offset from the axes of the numbered rings 11, 13 but parallel thereto so that the cog 12 can interact with both number rings 11, 13 which are housed in the substantially cylindrical part of the main body 5 without impeding axial movement of the container 10.

The main body 5 is provided at a lower end thereof with an axial protrusion 121 integral with the main body 5. The axial protrusion 121 comprises a hollow elongate portion into which the valve stem 22 of the container 10 can be received. The hollow portion is provided with a narrowed constriction against which the valve stem 22 can abut when the dispensing apparatus is actuated. The axial protrusion 121 protrudes from the lower end of the main body 5 as shown in FIG. 2. The axial protrusion 121 provides protection for the valve stem when the mouthpiece 20 has been removed. In particular with the mouthpiece 20 removed the valve stem 22 is not easily accessed as it is recessed relative to the distal end of the protrusion 121. This significantly reduces the chance that the container 10 could be actuated by direct pressure being applied to the end of the valve stem 22 which might circumvent the dose counter mechanism.

The main body 5 is provided with one or more slots 122 in an upper region for interaction with corresponding parts of the fixing collar 3 as described below.

Figure 15:
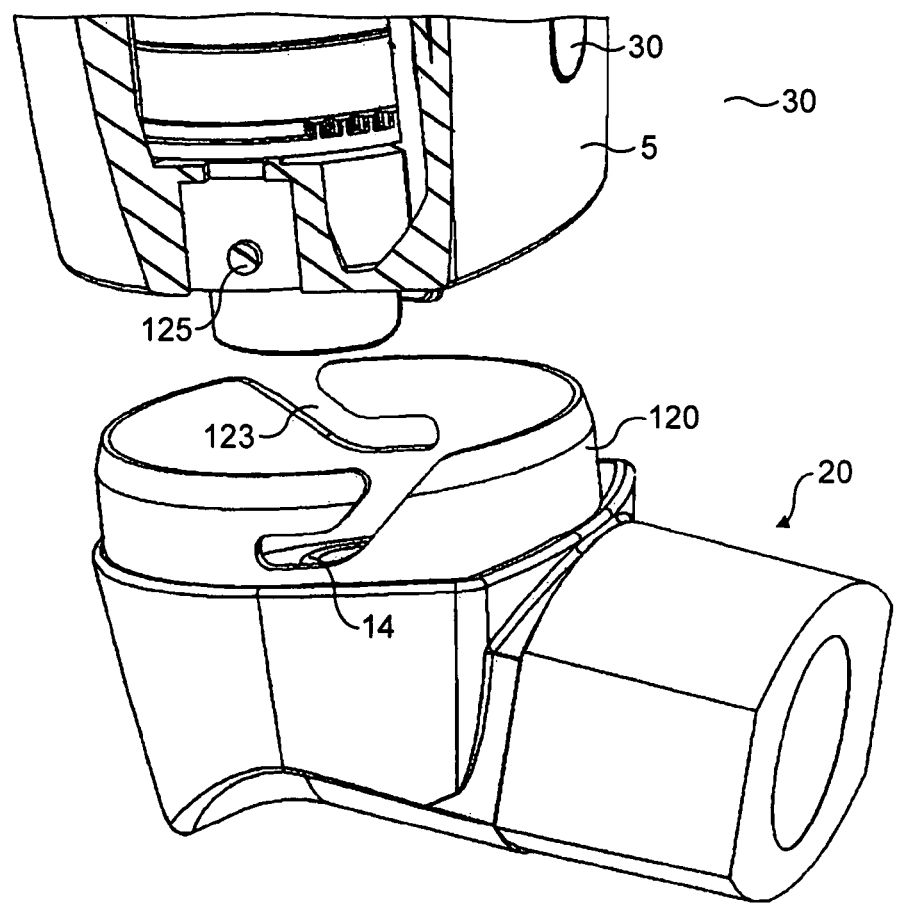
FIG. 15 is a perspective view of the dispensing apparatus of FIG. 8 with the mouthpiece detached and some parts shown in cross-section.

The detachable mouthpiece 20 is attached to the main body 5 by means of a bayonet fitting. FIG. 15 shows the bayonet fitting as applied to a second embodiment of apparatus as will be described below. However, the mouthpiece fitting is equally applicable to the first embodiment. As shown in FIGS. 2 and 15 the mouthpiece 20 is provided with an upstanding rim 120 in which are formed two opposed recesses 123 of roughly an L-shape configuration. The main body 5 comprises a circumferential recess 200 which receives the rim 120 when the two pieces are coupled together. At opposed points of the circumferential recess 200 the main body 5 is provided with retaining lugs 125 which pass along the recesses of the mouthpiece. Thus the mouthpiece may be coupled to the main body 5 by locating the lugs 125 relative to the upper end of the recesses and then twisting the main body 5 relative to the mouthpiece 20 whilst applying a compressive axial force to the two components. This results in the lugs 125 riding along the recesses resulting in the two components being firmly connected. Accordingly, it is very simple to change the mouthpiece of the dispensing apparatus, if desired or remove the mouthpiece for washing. The mouthpiece 20 is also provided with a spray block 14 for receipt of the axial protrusion 121. The spray block 14 comprises a conduit having an upper end which receives the axial protrusion 121 and a lower end which comprises a spray outlet directed towards the outlet of the mouthpiece 20. The spray outlet may be provided with a suitably dimensioned orifice or spray pattern block as known in the art to produce an atomised spray of product on dispensation.

Figure 7:
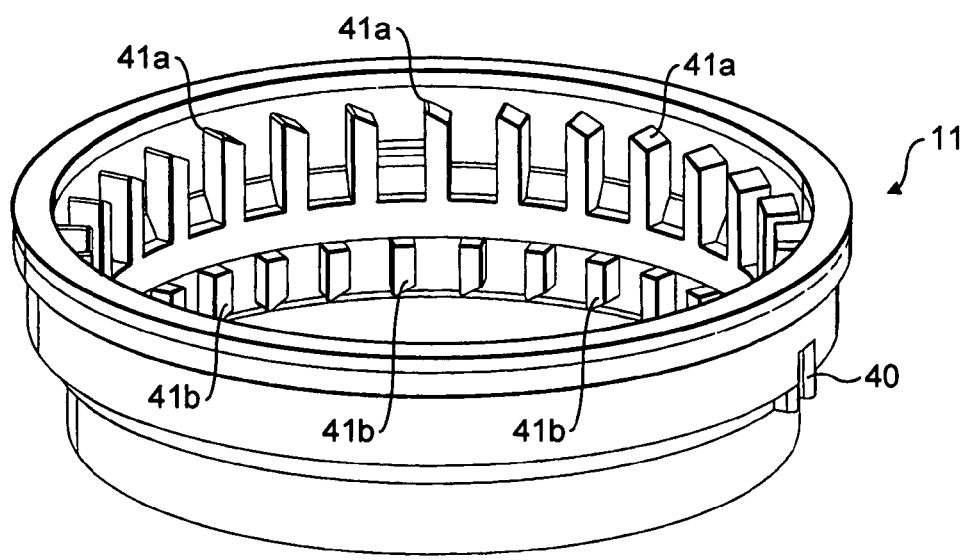
FIG. 7 is a perspective view of a first number ring having two different diameter portions, forming part of the dispensing apparatus of FIG. 1.
Figure 9:
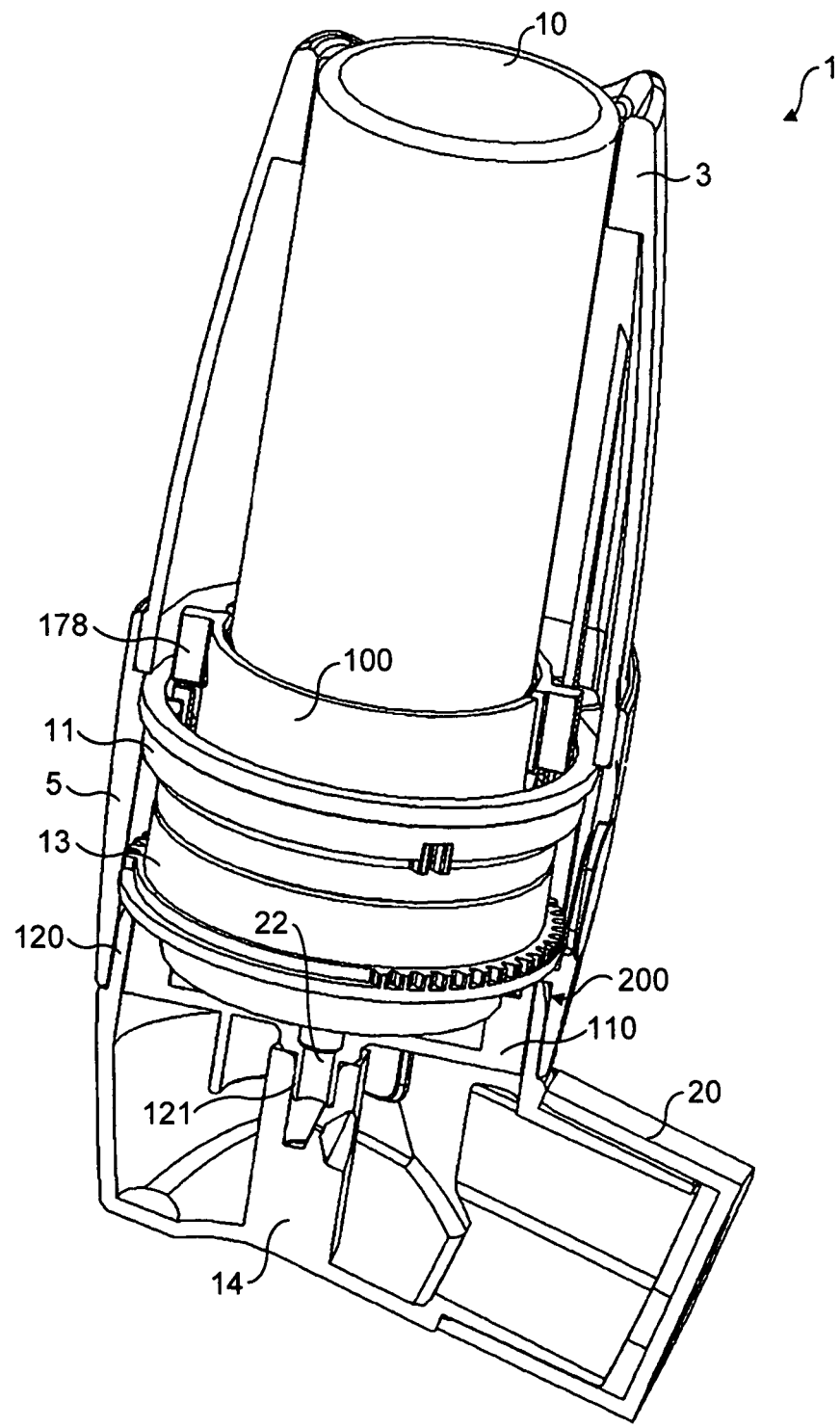
FIG. 9 is a cross-sectional view of the apparatus of FIG. 8.

The first number ring 11 is provided with two rows of angled abutment surfaces 41 located on two different diameter portions of that number ring as shown in FIG. 9. The angled abutment surfaces 41 of a larger diameter portion are indicated by reference 41a and those of a smaller diameter by reference 41b, as shown in FIG. 7, in particular. The first number ring 11 comprises at least one notch 40 positioned on the outer edge thereof. The first number ring 11 is also provided with a set of numbering (not shown in the drawings) from 0 to 9 for each notch 40, so that after the ninth actuation of the apparatus 1, the notch 40 is in position to interact with the cog 12. In a preferred embodiment, the number ring 11 will have three notches 40 and, so, will have three sets of numbering from 0 to 9.

The second number ring 13 is provided with an extended portion 150 which is positioned to enable covering of the markings on the first number ring 11 when a container locatable in the housing is empty. Advantageously, the extended portion 150 provides a clear indication to a user that the dispensing apparatus has provided its full-quota of dispensations.

Figure 4:
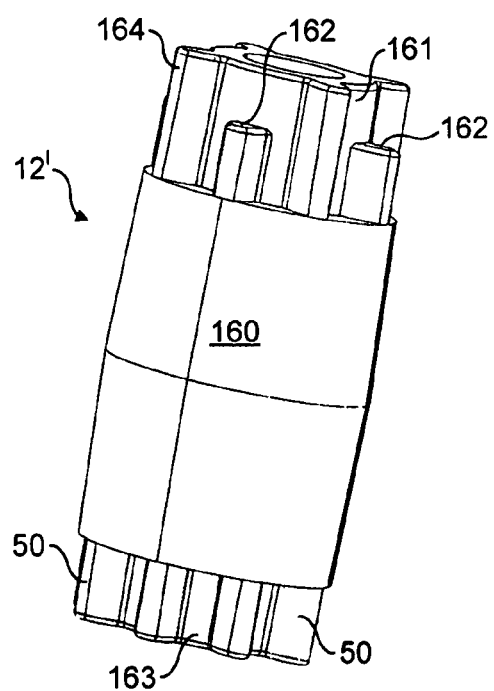
FIG. 4 is a perspective view of a cog forming part of the dispensing apparatus of FIG. 1.

The cog 12, as shown in FIG. 4 in particular, is provided with one or more teeth separated by a non-toothed spacer 160. A first end 161 of the cog 12 includes four teeth 162 of reduced height and four teeth 164 of full height which in use interact with the first annular member 11. The full height teeth 164 extend from the spacer 160 to the distal face of the first end 161 of the cog 12. The teeth 50 at a second end of the cog 12 are all full height and these teeth in use interact with the second annular member 13. The four teeth 162 having reduced height are, typically, half the height of the full height teeth 164. Most preferably, the reduced height teeth 162 and full height teeth 164 are arranged alternately around the circumference of the cog 12.

Figure 5:
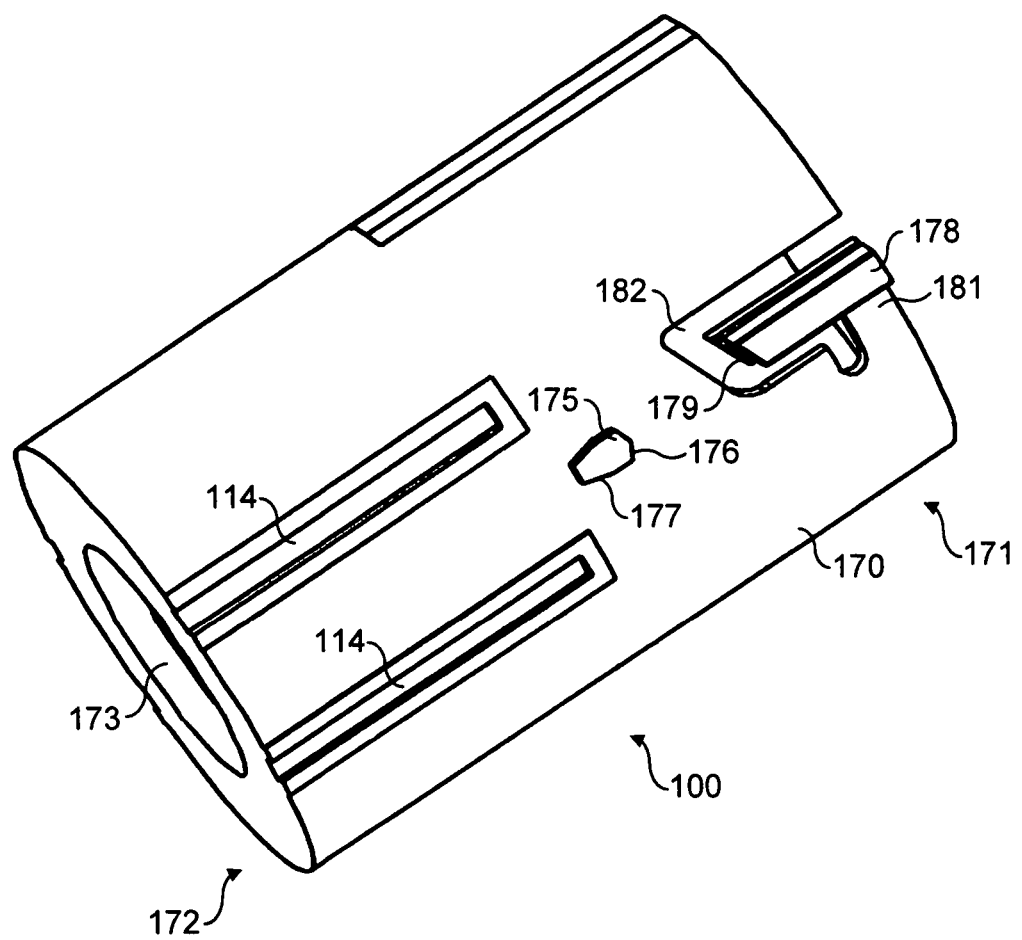
FIG. 5 is a perspective view of a sleeve forming part of the dispensing apparatus of FIG. 1.
Figure 6:
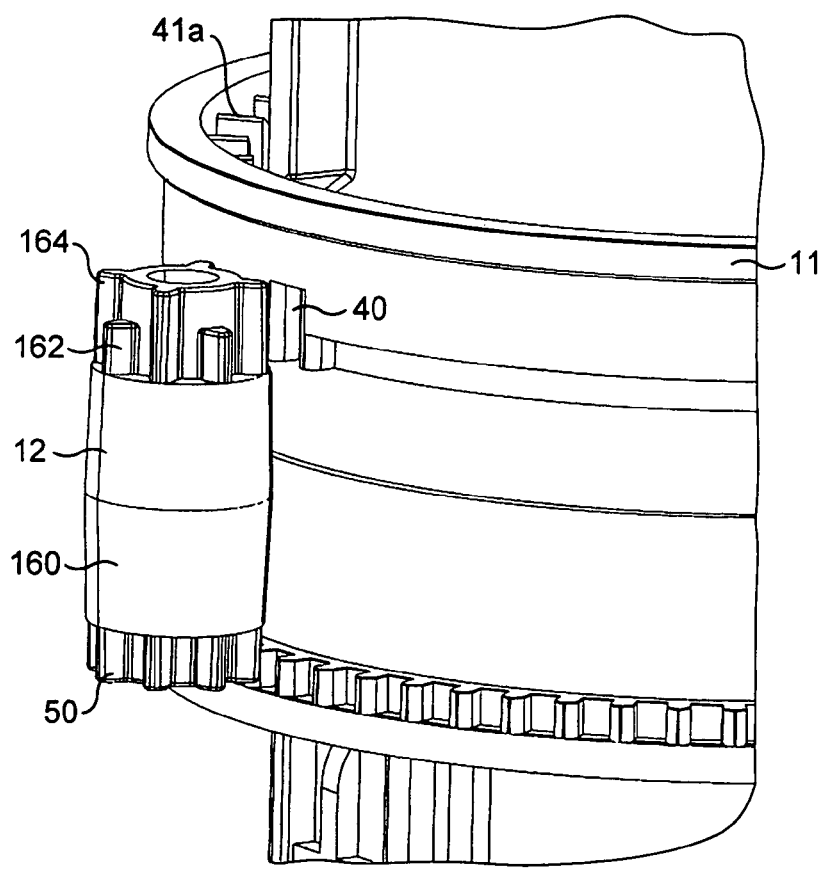
FIG. 6 is a perspective view of first and second number rings and a cog forming part of the dispensing apparatus of FIG. 1.

As shown in FIGS. 2 and 5, the sleeve 100 comprises an open-ended cylinder 170 having an upper end 171 which can receive the container 10 to be located in the dispensing apparatus 1 and a lower end 172 which has a reduced diameter opening 173 through which the valve stem 22 of the container 10, located within the sleeve 100 may protrude from but through which the body of the container 10 cannot pass. The sleeve 100 is provided with two sets of formations on its exterior surface. The sets of formations are arranged diametrically opposite one another (only one set of formations is shown in FIG. 5). Each set of formations comprises first, second and third formations. The first formation is provided at the lower end 172 in the form of longitudinally extending slots 114. The slots 114 may be formed as a recess in the surface of the sleeve 100 or defined as the space between two parallel ridges formed on the sleeve 100. The slots 114 extend from the lower end 172 to approximately the mid-point of the sleeve 100. The second formation is provided above the slots 114 in the form of a projection 175 having upper and lower angled abutment surfaces 176, 177. The third formation is provided at the upper end 171 in the form of a cantilevered projection 178. The cantilevered projection 178 comprises an elongated portion having an angled abutment surface 179 on its lower, distal end. The elongated portion of the cantilevered projection 178 is axially aligned with the projection 175. The elongated portion is joined to the cylindrical body of the sleeve 100 at a hinge point 181. A void space 182 is formed around the elongated portion to accommodate movement of the cantilevered projection 178 in use as will be described below.

As shown in FIG. 2, the cap 2 fits over the upper end of the container 10, opposite the metering valve. The cap 2 is provided with a plurality of external flange portions 130, for interaction with the fixing collar 3.

The fixing collar 3 is provided with one or more notches for locating in the one or more slots 122 of the main body 5, so as to provide an improved push-fit attachment of the fixing collar 3 to the main body 5. The fixing collar 3 is provided with internal flange portions 140, such that, the external flange portions 130 of the cap 2 interact with the internal flange portions 140 to retain the cap 2 and, therefore, the container 10, within the main body 5 when closed. The fixing collar 3 is provided with a clear portion 30, or one or more apertures 30 through which portions provided with markings of the number rings 11, 13 are visible. Preferably, the fixing collar 3 is provided with a projection 124 at the end of which is provided the clear portion 30 or one or more apertures 30. This projection 124 extends into the region of the main body 5 into a correspondingly-shaped hole 125. This arrangement provides the clear portion 30 or the one or more apertures 30 at a position in the region of the main body 5 which allows viewing of the markings on the number rings 11,13.

The fixing collar 3, in combination with the cap 2, provides a closure to the upper end of the main body 5, remote from the mouthpiece 20. In addition, the internal parts of the dispensing apparatus, for example, the number rings 11, 13, the cog 12, the sleeve 100, and the container are held within the main body 5 by the fixing collar 3 and the cap 2.

In use, a container 10 can be loaded into position within the apparatus 1 by separating the fixing collar 3 from the main body 5. The pressurised dispensing container 10 is first inserted into the sleeve 100 and the cap 2 positioned on an upper end of the container 10. The sleeve 100 is dimensioned so that the fit is a tight push-fit so that the container 10 is firmly retained in the sleeve 100. The sleeve 100 and container 10 sub-assembly is then inserted, valve stem 22 first, into the opening of the main body 5. The internal projections 110 of the main body 5 are received slidingly in the slots 114 of the sleeve 100 with the effect that the sleeve 100 is fixed rotationally relative to the main body 5. The valve stem 22 of the pressurised dispensing container 10 is received in the axial protrusion 121. Such loading inserts the sleeve 100 and dispensing container 10 through the central holes/apertures of the number rings 11, 13 and, when loaded, the number rings 11,13 are located around the container 10 as shown in FIG. 2. The fixing collar 3 is then fixed to the main body 5.

The apparatus 1 is actuated by depression of the cap 2 which protrudes upwardly from the fixing collar 3. Depression of the cap 2 causes the dispensing container 10 and sleeve 100 to move axially within the main body 5 to actuate the container 10. Actuation causes an amount of product to be dispensed from the container 10 by an opposite reaction force from the constriction in the axial protrusion 121 acting on the valve stem 22, which is inwardly retracted relative to the remainder of the metering valve such that an amount of product is dispensed from the valve stem 22 through the valve stem receiving block 14, from where it is dispensed as an aerosol through the mouthpiece 20 and inhaled by a user inhaling on the mouthpiece 20. Release of the cap 2 causes the cap 2 and the container 10 to return to its starting position, owing to the internal spring bias of the metering valve, ready for subsequent dispensing.

Each actuation of the apparatus 1 causes the first number ring 11 to rotate during the downstroke of the dispensing container owing to engagement of the angled abutment surface 179 of the cantilevered projection 178 with the angled abutment surfaces 41a the first number ring 11 and during the upstroke of the dispensing container owing to engagement of the angled abutment surfaces 176 if the projection 175 with the angled abutment surfaces 41b of the first number ring 11. Both rotations are in the same sense such that over the actuation cycle of one downstroke and one upstroke the first number ring 11 rotates by one increment. Angled abutment surfaces 177 of the projection 175 ease passing of the projection 175 past the upper surfaces of the lower teeth of the first number ring 11. Importantly, the force needed to rotate the first number ring 11 during a normal mode of operation is less than the force needed to flex the cantilevered projection 178 about the hinge point 181 sufficiently to allow the projection to bypass the teeth of the first number ring 11. Thus, normally the number ring 11 rotates rather than the cantilevered projection 178 being flexed.

Every ten actuations of the apparatus 1 cause the notch 40 to pass the cog 12, the effect of this being that one of the full height teeth 164 of the upper row of teeth is caught in the notch 40 as it rotates, this rotation causes a corresponding rotation of the cog 12 in the opposite sense. As a consequence, the second number ring 13 is caused to rotate in the same sense as the first number ring 11 by interaction of the teeth 50 on the bottom of the cog 12 and the teeth of the second number ring 13. Therefore, it can be seen that every actuation of the apparatus causes the value of the numbering visible through the one or more apertures 30 to be decreased or augmented by a value of one.

If the number rings 11, 13 or cog 12 become jammed or otherwise inoperative the dispensing apparatus can still be actuated as follows. On engagement of the angled abutment surface 179 of the cantilevered projection 178 against the angled surfaces 41a of the first number ring (which are now immobile) the elongated portion of the cantilevered projection flexes about the hinge point 181 so that the distal end of the elongate portion moves out of alignment with the angled surfaces 41a of the teeth of the first number ring. The cantilevered projection and hence the sleeve 100 as a whole can now move axially downwardly into the actuated position with the elongated portion of the cantilevered projection passing between a pair of the teeth 41 of the first number ring 11.

Another advantage of the use of the cantilevered projection 178 for incrementing the indexing mechanism is that it provides the dispensing apparatus with a mechanism for resisting sudden impacts. With some conventional mechanical dosage counters a problem can occur where the dispensing apparatus is dropped or otherwise suffers a sudden impact. This can cause damage to the indexing mechanism in particular damage to the relatively small teeth of the annular counter rings 11, 13. Another potential problem of sudden impacts is that this can cause the indexing mechanism to increment or decrement because the indexing member is held, in the unactuated position, in close proximity or in contact with the indexing mechanism. In the present invention the use of the cantilevered projection 178 provides a degree of inherent flexibility in the indexing member which allows the indexing member to absorb sudden impulses of force such as occur when the device is dropped without leading to damage of the mechanism or the mechanism in the form of the annular members 11, 13 being incremented or decremented. For example if the dispensing apparatus is dropped so as to impact on a hard surface with the mouthpiece lowermost, the force impulse is transmitted upwardly through the main body 5 into the annular members 11, 13. The force impulse is then transmitted from the annular members to the cantilevered projection 178. However, at this point the cantilevered projection 178 is able to flex upwardly sufficiently to absorb the impulse without the effect that the upper annular member is damaged or rotated relative to the cantilevered projection. Thus, the inherent flexibility of the cantilevered projection 178 and the fact that a void space 182 is provided around it to accommodate movement of the cantilevered projection 178, provides the dispensing apparatus with a mechanism for coping with impact forces without suffering damage or indexing the indexing mechanism.

FIGS. 8 to 14 illustrate a second embodiment of dispensing apparatus according to the present invention in which certain components have been modified. In the following description, only the parts that differ in structure or use are described in detail. Other parts which function in the same way as described in the first embodiment will not be described any further and reference is directed to the description of that embodiment.

Figure 8:
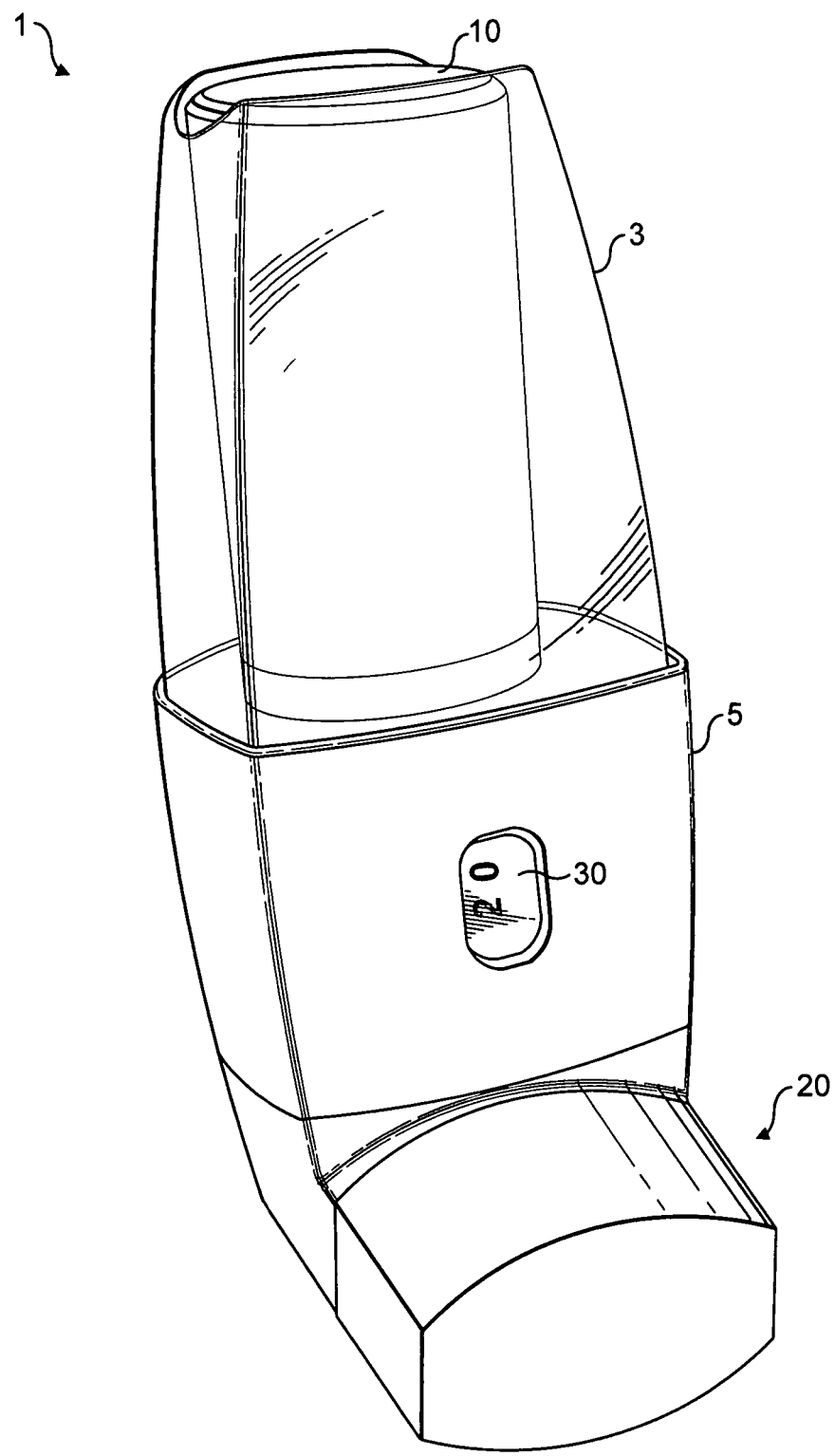
FIG. 8 is a perspective view of a second embodiment of dispensing apparatus according to the present invention.

As shown in FIG. 8, the apparatus 1 comprises a lower body 5 and an upper body 3 which may be transparent. A detachable mouthpiece 20 is again provided which is shown in FIG. 15 and is described above. The first and second number rings 11, 13 and cog 12 are housed in the lower body 5 together with the sleeve 100. The upper body 3 is open at its upper end and does not comprise a cap. The opening in the upper body 3 is sized such that the sleeve 100 cannot pass therethrough but so that the container 10 is able to pass through.

In the second embodiment, as shown in FIGS. 9 and 13, the sleeve 100 is modified. Firstly, the slots of the first embodiment are replaces by a pair of notches 114 in the lower end of the sleeve 100. Secondly, the formation of the projection 175 of the first embodiment is replaced by a tension arm 300. Preferably two tension arms 300 are provided at opposed points of the sleeve 100. As with the projection 175 of the first embodiment, the tension arm 300 is located longitudinally between the notches 114 and the cantilevered projection 178. The tension arm 300 comprises a cantilevered portion 301 which is fixed to the sleeve 100 at a hinge point 302. Preferably, the tension arm 300 is provided in a single moulding as part of the sleeve 100 in which case the hinge point 302 marks the junction between the body of the sleeve 100 and the start of the cantilevered portion 301 of the tension arm 300. A distal end 303 of the tension arm 300 is provided with an outwardly directed projection 304. It can be seen from FIG. 13 that the cantilevered tension arm 300 is able to accommodate flexure in a direction perpendicular to flexure of the cantilevered projection 178. That is, the outwardly directed projections 304 of the tension arm 300 can flex substantially radially inwards when pressure is applied to the projections in a radially inward direction. It will be appreciated that the shape of the container 10 must accommodate inward flexure of the tension arms 300. It is therefore preferable that the position of the tension arms 300 be located to coincide with the neck of the container 10 where it narrows to meet the ferrule of the metering valve, as shown in FIG. 9. It will therefore be apparent that the overall length of the sleeve 100 is less than in the first embodiment. Alternatively, the walls of the container 10 may have formed in them depressions to accommodate inward flexure of the tensions arms 300.

Figure 10:
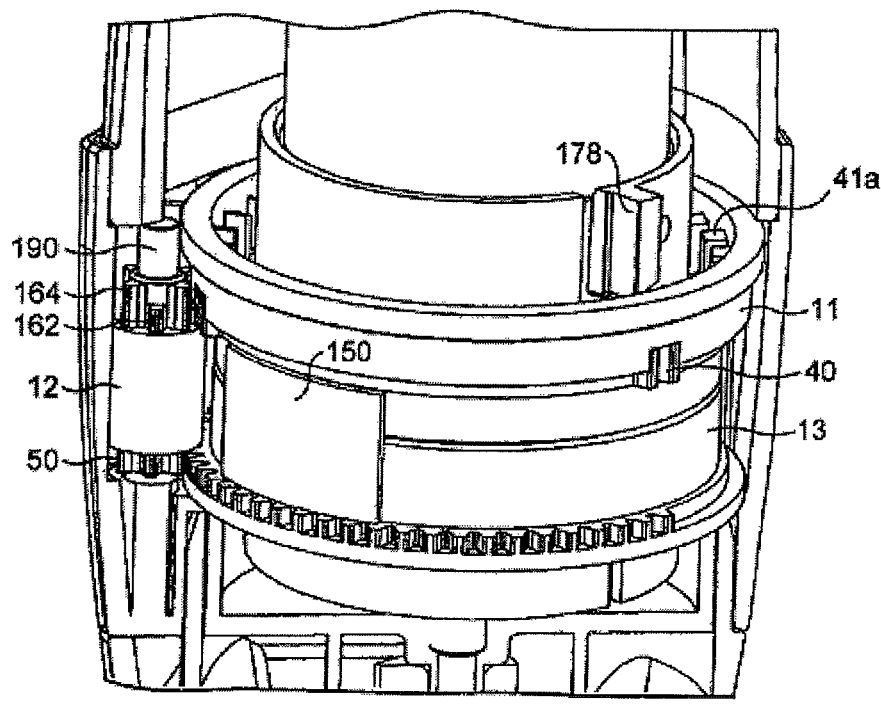
FIG. 10 is a perspective view of various internal features of the dispensing apparatus of FIG. 8.
Figure 11:
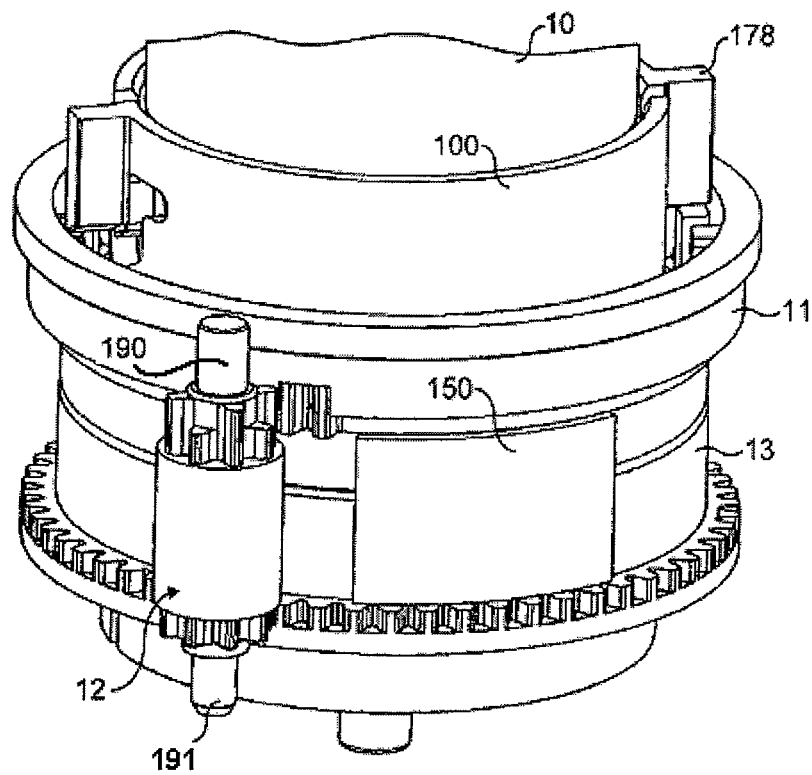
FIG. 11 is a perspective view of first and second number rings and a cog forming part of the dispensing apparatus of FIG. 8.

As shown in FIGS. 10 to 12, the cog 12 is slightly adapted compared to the first embodiment. The spacer 160 is cylindrical. In addition, the cog 12 is provided with upper and lower axial projections 190 and 191 which allow the cog 12 to be rotationally mounted in recesses formed in the lower body 5 as shown in FIG. 10.

Figure 14:
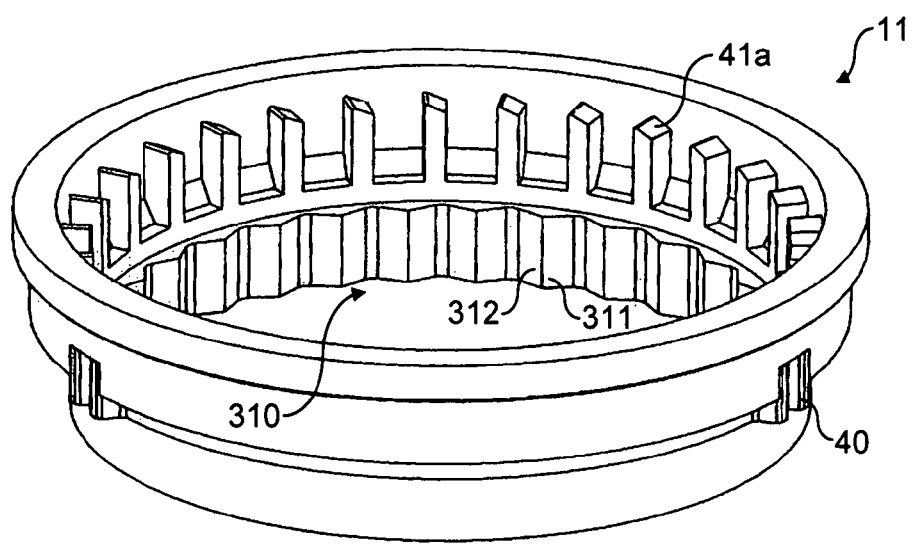
FIG. 14 is a perspective view of a first number ring having two different diameter portions, forming part of the dispensing apparatus of FIG. 8.

FIG. 14 illustrates first number ring 11 of the second embodiment. It will be seen that the number ring 11 differs from that in the first embodiment only to the degree that the lower set of angled abutment surfaces 41b formed on the smaller diameter portion of the ring are replaced by a series of inwardly directed projections 310 having a triangular cross-section when viewed from above. The projections 310 are arranged around the circumference of the lower portion of the ring 11 so as to form a series of interspersed peaks and troughs. Each projection 310 comprises two faces 311, 312 on either side of the peak. Preferably, the faces 311, 312 are arranged symmetrically about the peak. The faces 311 and 312 form angled abutment surfaces which engage the outward projection 304 of the tension arm 300 in use as will be described below.

In use, the internal components of the apparatus, such as the cog 12, the sleeve 100 and the number rings 11, 13 can be loaded into position within the apparatus 1 by separating the upper body 3 from the lower body 5. The sleeve 100 can be inserted, valve stem 22 first, into the opening of the lower body 5. The internal projections 110 of the lower body 5 are received slidingly in the notches 114 of the sleeve 100, as shown in FIG. 9, with the effect that the sleeve 100 is fixed rotationally relative to the lower body 5. The valve stem 22 of the pressurised dispensing container 10 is received in the axial protrusion 121. The sleeve 100 is arranged to pass through the central holes/apertures of the number rings 11, 13 and, when loaded, the number rings 11,13 are located around the container 10 as shown in FIG. 9. The collar 3 is then attached to the main body 5.

Figure 16:
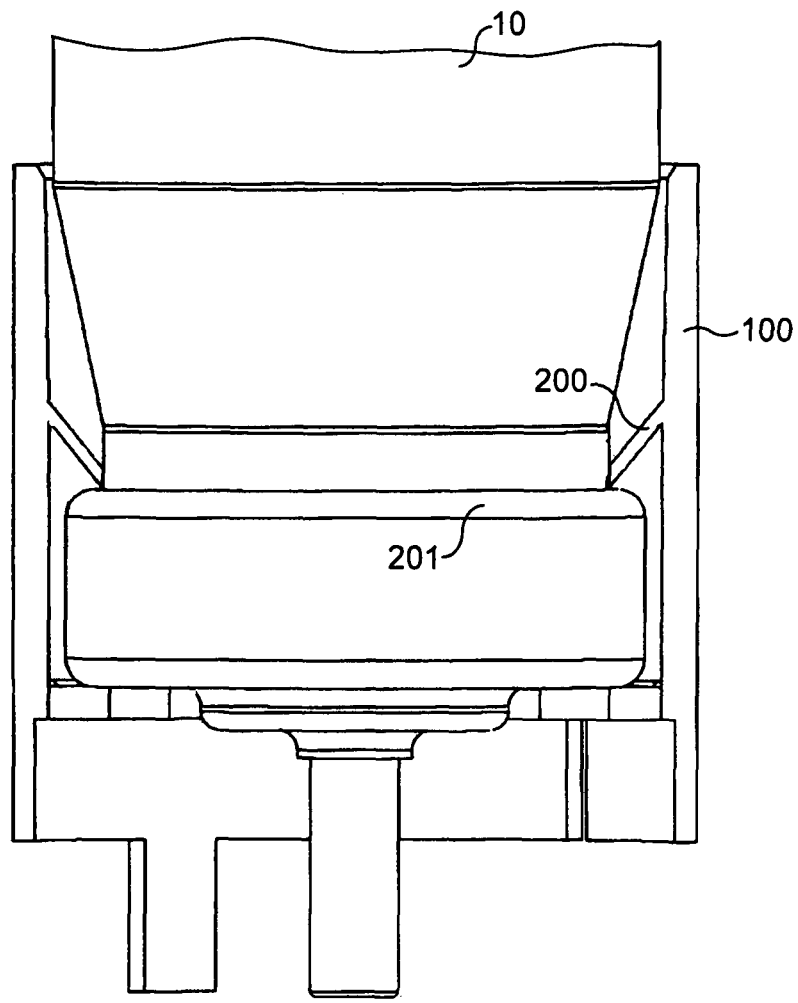
FIG. 16 is a schematic view of part of the apparatus of FIG. 8 with some parts omitted for clarity.

The pressurised dispensing container 10 can now be passed through the hole in the upper body 3 to be received in the sleeve 100. The internal face of the sleeve 100 is provided with a non-return feature 200, shown schematically in FIG. 16. The non-return feature 200 is preferably in the form of a flexible flange 200 which protrudes inwardly and in a downwards direction. As the container 10 is inserted into the sleeve 10 the flange 200 is deflected outwardly to allow a ferrule 201 of the container 10 to pass. Once in the assembled position the flange 200 springs back outwardly to engage in an undercut formation formed between the ferrule 201 and the body of the container 10 as shown in FIG. 16. In this way removal of the container 10 from the sleeve 100 is prevented.

In the inserted position the upper end of the container 10 protrudes upwardly through the hole in the upper body 3. Once assembled, the sleeve 100 passes within the first number ring 11 as in the first embodiment. The arrangement is shown in FIG. 9.

On actuation of the apparatus 1, downward movement of the sleeve 100 relative to the first number ring 11 brings the angled abutment surface 179 of the cantilevered projection 178 into contact with the angled abutment surfaces 41a of the upper teeth of the first number ring 11 as described above in the first embodiment. Thus, as in the first embodiment, during the down stroke of the sleeve 100 the first number ring 11 is rotated a partial increment by interaction of the angled abutment surface 179 with the angled abutment surfaces 41a of the first number ring 11. This partial rotation of the first number ring 11 causes each outwardly directed projection 304 of each tension arm 300 to ride up an angled face 311 of respective protrusions 310. This movement is accommodated by the tension arms 300 as they flex radially inwards. The relative location of the angled abutment surfaces 41a and the projections 310 is such that when the down stroke of the sleeve 100 is completed the outwardly directed projections 304 of the tension arms 300 have ridden up the angled abutment surfaces 311 and over the peak of the projections 310 such that the outwardly directed projections 304 lie in contact with the angled abutment surfaces 312 of the projections 310. Thus, when the container is released, and the sleeve 100 consequently moves back on its up stroke, the completion of the incremental rotation of the first number ring 11 is achieved by the biasing force of the outwardly directed projections 304 of the tension arms 300 on the angled abutment surfaces 312 as the tension arms 300 try to return to their unstressed position. This biasing force completes the rotation of the first number ring 11 such that the outwardly directed projections 304 of the tension arms 300 lie in the neighbouring trough between the projections 310 after one actuation. Consequently, the cantilevered projection 178 and the tension arm 300 (or the pairs of these features where present) act as first and second indexing members which together act to index the counter mechanism.

The indexing mechanism of the second embodiment has a particular advantage over the indexing mechanism of the first embodiment. The indexing mechanism of the second embodiment is better able to cope with the manufacturing tolerances of the components. In the first embodiment, in order to ensure that the indexing mechanism is incremented at the right point it is necessary to control the longitudinal position of the cantilevered projection 178 relative to the projection 175 as well as the relative longitudinal positions of the cantilevered projection 178 with the features of the axial protrusion 121 which receives the valve stem in use. Not only this it is necessary to control the longitudinal position of the projection 175 relative to the features of the axial protrusion 121. In the second embodiment, the longitudinal position of the projections 310 is not a determinative, critical tolerance since the longitudinal location of the projections 310 does not affect operation of the indexing mechanism as long as the projections 310 extend upwardly and downwardly enough to remain in contact with the outwardly directed projections 304 of the tension arms 300 in use. Thus, by ensuring that the projections 310 have sufficient depth the specific longitudinal location of the outwardly directed projections 304 relative to the projections 310 in the unactuated position is not a critical tolerance. This may be seen by noting that the cantilevered projection 178 and the tension arm 300 act along different axes—the first longitudinally relative to the sleeve and the second radially to the sleeve. Thus the relative longitudinal position of these two features is not critical. This results in the manufacture of the device being significantly simplified.

Another advantage is that the container 10 and sleeve 100 may more easily return to the unactuated position when the container 10 is released compared to the first embodiment. In the first embodiment the internal spring bias of the metering valve must overcome the friction caused by contact between the projection 175 and the angled abutment surfaces 41b which is relatively high. In the second embodiment the degree of friction caused by contact between the outwardly directed protrusions 304 and the projections 310 is much less as the contact face is parallel to the direction of movement of the sleeve 100.

The remainder of the operation of the apparatus, for example the manner in which the first number ring 11 interacts with the second number ring 13 is the same as in the first embodiment described above.

In the first embodiment it has been described that the apparatus comprises a cap 2 to close off an upper end of the apparatus. It will be appreciated that the presence of the cap 2 is not essential to the working of the apparatus. In particular, if removal of the container 10 is to be prevented then other mechanisms may be provided other than the cap 2 without departing from the scope of the present invention as indicated in the second embodiment.

It will be appreciated that since the second embodiment still retains the cantilevered projection 178 as part of the indexing mechanism then the advantages of impact resistance as described above in the first embodiment will apply equally to the second embodiment.

Whilst in the specific example details of the invention are discussed, it will of course be understood that minor variations in features are still considered to be covered by the same inventive concept.

In an alternative embodiment, the dispensing apparatus may comprise, say, three or more number rings: a first number ring for 'units', a second for 'tens' and a third for 'hundreds'. Further cogs may be provided. Subsequent number rings for 'thousands' and so on may also be added. The second and subsequent number rings are rotated by an arrangement as described herein (by a cog rotated by a previous number ring), whereby ten incremental rotations of the previous number ring—as started originally on the 'units' number ring by actuation of the apparatus—causes an incremental rotation of the subsequent number ring.

The invention has been described by way of example with the indexing member moving relative to the indexing mechanism in order to achieve bypass in the event of jamming of the apparatus. The preferred option is that the indexing member moves by means of flexing or otherwise being distorted relative to its unloaded configuration. It will be appreciated that the indexing member may be designed to pivot about a hinge point rather than flex. For example the hinge point could be provided with a spring element, such as a torsion spring, to allow pivoting only when a load threshold indicative of a jammed apparatus is exceeded. Alternatively, the indexing member may be sprung and be enabled to retract in a sliding manner relative to the sleeve 100 or shift sideways relative to the direction of movement of the sleeve 100 to allow the sleeve to move when the apparatus is jammed. Again, the spring force of the biasing means may be chosen to allow movement of the indexing member relative to the sleeve only when a jammed condition occurs.

The indexing member has been illustrated as being flexible about a single pivot point 181. However the indexing member may be designed to have two pivot points forming a parallelogram four-bar mechanism. The flexible portion of the indexing member make take a number of forms including an arcuate portion having a serpentine configuration.

Finally, it will be appreciated that the indexing mechanism may be designed to move or flex relative to the indexing member as an alternative solution. For example, the teeth of the first and/or second number rings 11, 13 may be designed to have a degree of inherent elasticity which would allow a rigid indexing member to bypass by displacing or distorting the teeth if a jammed condition was encountered.

The invention claimed is:

1. Dispensing apparatus for delivering metered doses of product from a pressurised dispensing container comprising:
    a housing for receiving a pressurised dispensing container;
    a dose counting mechanism comprising indication means for displaying to a user an indication associated with the number or quantity of doses dispensed from, or the number or quantity of doses remaining in, the received pressurised dispensing container;
    the dose counting mechanism further comprising an indexing mechanism for advancing the indication means on actuation of the received pressurised dispensing container;
    wherein the dispensing apparatus comprises first and second indexing members which together act to incrementally advance the indexing mechanism on actuation of the received pressurised dispensing container;

wherein the indexing mechanism comprises a first set of abutment surfaces for engagement with the first indexing member and a second set of abutment surfaces for engagement with the second indexing member;

wherein movement of the received pressurised dispensing container in a first direction relative to the indexing mechanism causes the first indexing member to advance the indexing mechanism by a partial increment by engagement of the first indexing member with the first set of abutment surfaces and also causes a strain to be imparted on the second indexing member;

wherein subsequent movement of the received pressurised dispensing container in a second direction, opposed to the first direction, allows the second indexing member to move the indexing mechanism by engagement with the second set of abutment surfaces to complete the incremental advancement of the indexing mechanism by recovery of the imparted strain.

2. Dispensing apparatus as claimed in claim 1 wherein the strain imparted on the second indexing member is in a direction substantially perpendicular compared to the direction of movement of the first indexing member.

3. Dispensing apparatus as claimed in claim 1 wherein the first indexing member is moveable parallel to the longitudinal axis of the received pressurised dispensing container.

4. Dispensing apparatus as claimed in claim 1 wherein the strain imparted on the second indexing member is in a radial direction relative to the received pressurised dispensing container.

5. Dispensing container as claimed in claim 1 wherein the first indexing member comprises a cantilevered portion having a free distal end which interfaces in use with the indexing mechanism.

6. Dispensing apparatus as claimed in claim 5 wherein the cantilevered portion of the first indexing member comprises an elongate portion running parallel to the longitudinal axis of the received pressurised dispensing container.

7. Dispensing container as claimed in claim 1 wherein the second indexing member comprises a cantilevered portion having a free distal end which interfaces in use with the indexing mechanism.

8. Dispensing apparatus as claimed in claim 7 wherein the cantilevered portion of the second indexing member comprises an arcuate portion running around the longitudinal axis of the received pressurised dispensing container.

9. Dispensing apparatus as claimed in claim 1 wherein a distal end of the second indexing member comprises an outwardly directed projection for engaging the indexing mechanism.

10. Dispensing apparatus as claimed in claim 1 wherein the indexing mechanism comprises an annular member.

11. Dispensing apparatus as claimed in claim 10 wherein the first and second sets of abutment surfaces are provided on the annular member.

12. Dispensing apparatus as claimed in claim 11 wherein the second set of abutment surfaces are formed by a circumferential series of inwardly directed projections of the annular member.

13. Dispensing apparatus as claimed in claim 12 wherein the series of inwardly directed projections comprises interspaced peaks and troughs defined by the abutment surfaces.

14. Dispensing apparatus as claimed in claim 12 wherein a distal end of the second indexing member comprises an outwardly directed projection for engaging the second set of abutment surfaces.

15. Dispensing apparatus as claimed in claim 1 further comprising a sleeve for receiving in use the pressurised dispensing container.

16. Dispensing apparatus as claimed in claim 15 wherein the first and second indexing members are joined to or formed as part of the sleeve.

17. Dispensing apparatus as claimed in claim 1 wherein the first and or second indexing members are formed of an elastic material such that imparted strains during normal actuation are recoverable elastically.

18. Dispensing apparatus as claimed in claim 1 wherein the second indexing member is continuously in contact with the second set of abutment surfaces.

* * * * *